United States Patent [19]

Kellam

[11] Patent Number: 5,778,878

[45] Date of Patent: Jul. 14, 1998

[54] LASER DOPPLER MICROSCOPY METHODS AND INSTRUMENTS

[76] Inventor: Keith Kellam, Braeside, Smallridge, Axminster, Devon, EX13 7JJ, England

[21] Appl. No.: 451,771

[22] Filed: May 26, 1995

[30] Foreign Application Priority Data

Jun. 4, 1994 [GB] United Kingdom ............... 9411231

[51] Int. Cl.[6] .................................................. A61B 6/00
[52] U.S. Cl. .......................... 128/664; 128/691; 128/633
[58] Field of Search .................................. 128/691, 633, 128/666, 665, 661.08, 664, 653.1

[56] References Cited

U.S. PATENT DOCUMENTS

| 4,590,948 | 5/1986 | Nilsson | 128/666 |
| 4,651,226 | 3/1987 | Motoori et al. | 358/293 |
| 4,848,897 | 7/1989 | Aizu et al. | 128/691 |
| 5,361,769 | 11/1994 | Nilsson | 128/666 |
| 5,437,274 | 8/1995 | Khoobehi et al. | 128/633 |
| 5,501,226 | 3/1996 | Peterson et al. | 128/691 |

Primary Examiner—Brian L. Casler
Attorney, Agent, or Firm—Omri M. Behr, Esq.

[57] ABSTRACT

The velocity of blood cells in skin or other tissue capillaries is determined by a laser Doppler technique. A laser beam is focussed on to a capillary by means of a lens, mirror and beam splitter system and measurement of the velocity of the blood cells in a direction substantially perpendicular to the surface of the tissue is effected by detecting directly back-scattered radiation.

5 Claims, 7 Drawing Sheets

LASER DOPPLER MICROSCOPY METHODS AND INSTRUMENTS

FIELD OF THE INVENTION

This invention relates to laser Doppler microscopy methods and instruments.

Laser Doppler microscopy techniques are being used increasingly for research purposes.

A paper entitled "A laser Doppler microscope-Its optical and signal-analysing systems and some experimental results of flow velocity" was presented at the Laser Doppler Anemometry Symposium 1975 in Copenhagen by H. Mishina, T. Ushizaka and T. Asakura and published in the June 1976 issue of "Optics and Laser Technology".

This paper contains a description of the use of a laser Doppler microscope to obtain measurements of velocity in a biological field, in particular the velocity of the blood cells flowing in a venule and in a capillary over the web of a frog's foot. The work described in the paper indicates the capability of measuring the velocity of blood cells in the specific circumstances described in the paper.

The technique described by Mishina et al. does not, however, enable the rate of flow of blood through the capillaries of human skin to be measured in a non-invasive manner.

It is accordingly an object of the present invention to provide improved methods and instruments for the carrying out of laser Doppler microscopy techniques, particularly for the carrying out of measurements of blood cell velocity through skin capillaries in a non-invasive manner.

In U.S. Pat. No. 4,142,796 (Riva), there is described a measurement system in which a beam of laser light is impinged on blood vessels in the retina. This system is applicable, however, only to measurements of flow in relatively large vessels, such as are found in the retina, but not to the measurement of blood cell velocity in a capillary.

Other types of apparatus for measuring the flow of blood by a laser Doppler technique are described in U.S. Pat. Nos. 4,109,647; 4,166,695 and 4,590,948.

SUMMARY OF THE INVENTION

According to a first aspect of the present invention there is provided a method for the determination of the velocity of blood cells in a capillary in a tissue, for example, skin tissue, by a laser Doppler technique which includes measuring the velocity of the blood cells in a direction substantially perpendicular to the surface of the tissue by detecting directly back-scattered laser radiation.

The light generated by a laser source is preferably focussed by a lens system, which may include two lenses, to a spot size of the order of 10 microns in diameter. A CCD camera is preferably employed and is focussed so that the object plane and the laser focal point are the same.

The blood cells travelling with a velocity component perpendicular to the skin surface will, in effect, form an erythrocyte column moving with a velocity component perpendicular to the object plane so that the laser radiation will be reflected with a Doppler shift. An advantage of the perpendicular column is that the number of blood cells contributing to the back scatter is increased, thus increasing the strength of the detected signal. The 'sample volume', where the intensity of the laser beam is high enough to obtain enough back scatter, is much longer than it is wide. Also, all the contributing blood cells will be travelling at substantially the same velocity.

This is in contrast with a system, such as that of Riva referred to above, which measures velocity in vessels lying parallel to the surface and in which only the cells across the width of the vessel are able to contribute to the system. With a wider vessel, the Doppler shift is broadened since there will now be blood cells travelling at different velocities across the diameter of the vessel. More complex processing algorithms are then required.

In accordance with a further feature of the present invention, the Doppler-shifted radiation is preferably collected by the lens system and focussed on to a photodetector via two beam splitters and two mirrors. At the same time, some of the radiation will also be back-scattered by some of the surrounding tissue and this back-scattered radiation will also be collected by the objective lens and focussed on to the detector. In the photodetector, the autodyne mixing of these two optical signals will then produce an electrical signal where the frequency of the accomponent is directly proportional to the blood cell velocity.

The electrical signal from the photodetector is preferably amplified and filtered (50 Hz to 50 kHz bandpass) and then fed to an ADC (Analogue to Digital Converter), the output of which is buffered in a FIFO (First In First Out Buffer) which, together with the associated logic is on a standard bus circuit board which is installed in an IBM AT/PC compatible computer. The software preferably takes the digitised data and performs an FFT (Fast Fourier Transformation) from which the power spectrum is computed and the frequency of the peak in the power spectrum, or the maximum frequency above a certain power threshold, is detected and used to calculate the velocity of the blood cells in a selected capillary.

It is to be noted that the use of a FIFO is a means of relieving the computer software from the burden of collecting the data from the ADC at the signal sample rate, which may be variable up to 100 kHz. The software thus only has to collect blocks of samples, typically 512 samples every 0.05 seconds. The computer software can then process one block of data whilst the FIFO collects the next block.

According to a second aspect of the present invention there is provided an instrument for use in the determination of blood cell velocity in a capillary in a tissue by a laser Doppler technique, said instrument comprising means for generating a laser beam, means for directing the laser beam on to a surface of the tissue so as to impinge on a capillary within which blood cells are travelling with a component of velocity substantially perpendicular to the surface of the tissue, a camera for observing impingement of the laser beam on the skin surface and means for measuring the blood cell velocity by detecting directly back-scattered laser radiation.

As set out above, the laser beam is preferably focussed by a lens system, which may include two lenses, to a spot size of the order of 10 microns in diameter and the camera is preferably a CCD camera which is focussed so that the object plane and the laser focal point are the same.

The arrangement may be such that, if more than one measurement site is selected, the laser beam can be moved from one site to the next, only resting at each site long enough to record a measurement. Two stepping motors may be used to move the laser beam along the x and y directions independently. The motors may be arranged to rotate a single mirror in a gimbals-type mount via cams.

DESCRIPTION OF THE PREFERRED EMBODIMENTS

Figure 1:
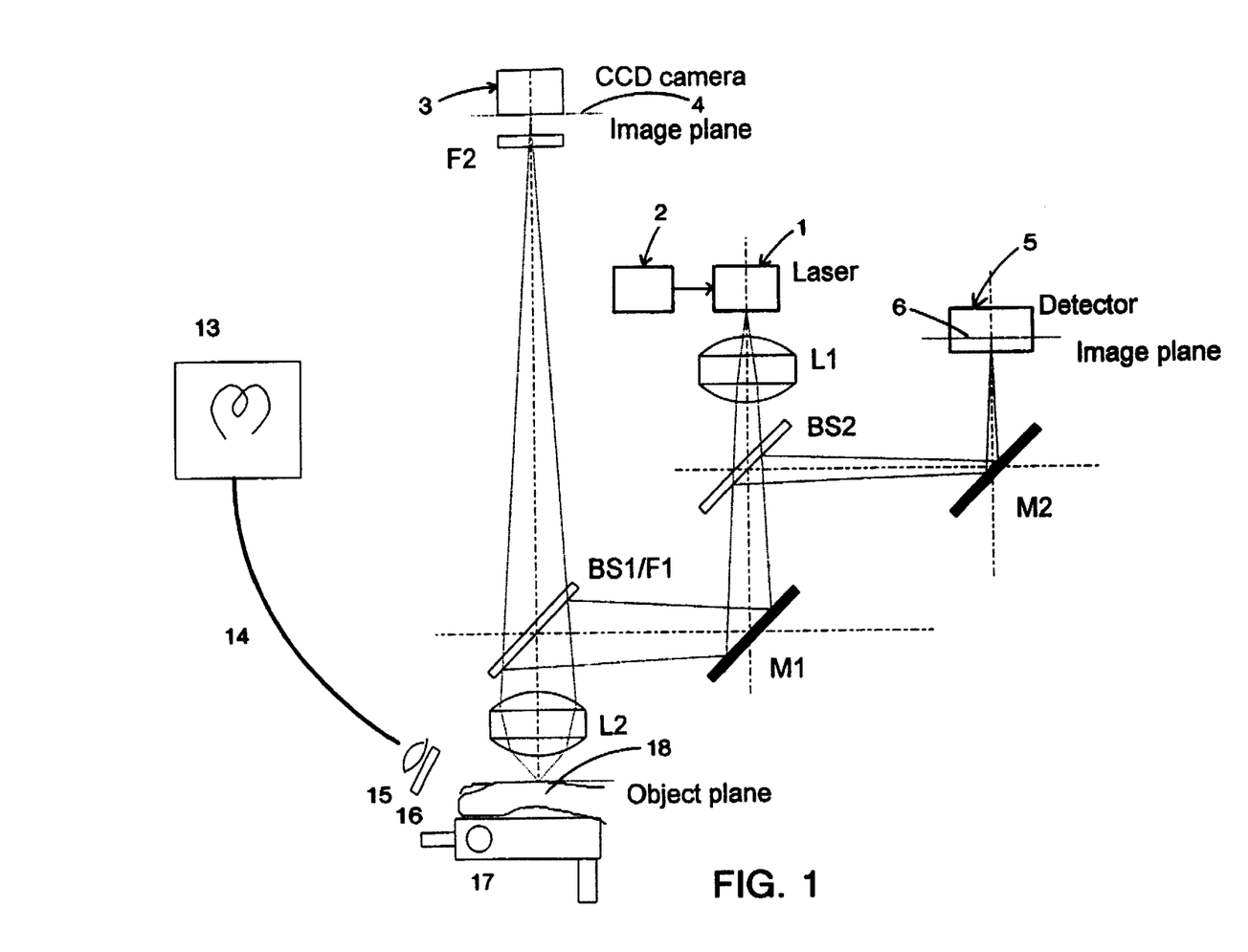
FIG. 1 is a schematic representation of an instrument for use in measuring capillary blood cell velocity.
Figure 2:
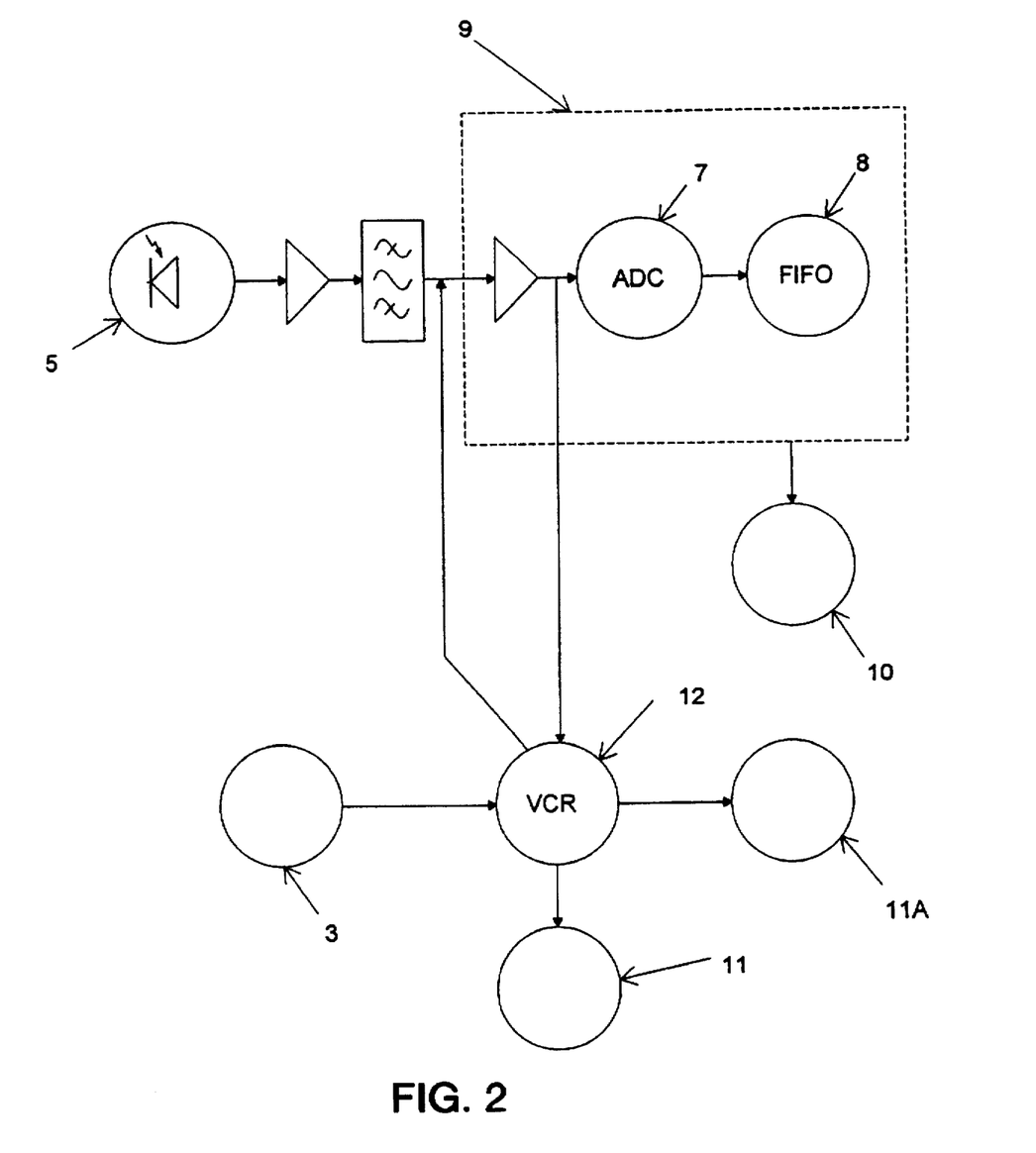
FIG. 2 is a block diagram of part of the instrument shown in FIG. 1.

The instrument shown in FIG. 1 includes a 10 Mw 780 nm Sharp LT027 laser diode 1 which is driven by a constant current source 2 so as to keep a constant power output even with changes in reflectance from the object and internal optics. Any other low-noise, single-mode laser could alternatively be employed as long as it had sufficient power. A near infra red laser is preferred since it is easier to separate it out from the camera spectrum, and silicon photodiodes are most sensitive in this range. The instrument includes a CCD camera 3 having an image plane 4 and a photodetector 5 having an image plane 6.

The power output of the laser diode 1 may vary with temperature. Temperature control of the laser diode 1 may, therefore, be provided. Alternatively, the laser diode temperature may be monitored and the drive current adjusted accordingly.

The laser beam is focussed to a spot at the object plane by a pair of lenses L1 and L2. Lens L1 is a plano-convex lens having a focal length of, for example, 20 mm. and lens L2 is a microscope objective lens. The laser beam passes through a beam splitter BS2 and is reflected by a mirror M1 and by a beam splitter BS1/F1. The beam splitters BS2 and BS1/F1 are so chosen as to obtain an optimum signal to noise ratio for both the camera 3 and the photodetector 5. Beam splitter BS1/F1 also acts as a filter.

The laser beam impinges on the subject under examination. As shown, the subject is a finger. The reflected laser radiation is collected by lens L2 and focussed via beam splitter BS1/F1, mirror M1, beam splitter BS2 and a second mirror M2 on to the photodetector 5 which is in the form of a 1 mm.×1 mm. PIN photodiode. The active area (or aperture in the image plane 6) can be optimized for the best signal to noise ratio. The output of the photodetector or photodiode 5 is amplified, bandwith limited and then passed to an ADC (Analogue to Digital Converter) 7. The output of the ADC 7 is buffered in a FIFO (First In First Out Buffer) 8. The ADC 7 and the FIFO 8, together with the associated logic, are on an industry standard bus circuit board installed in an IBM AT/PC compatible computer 9.

Figure 7:
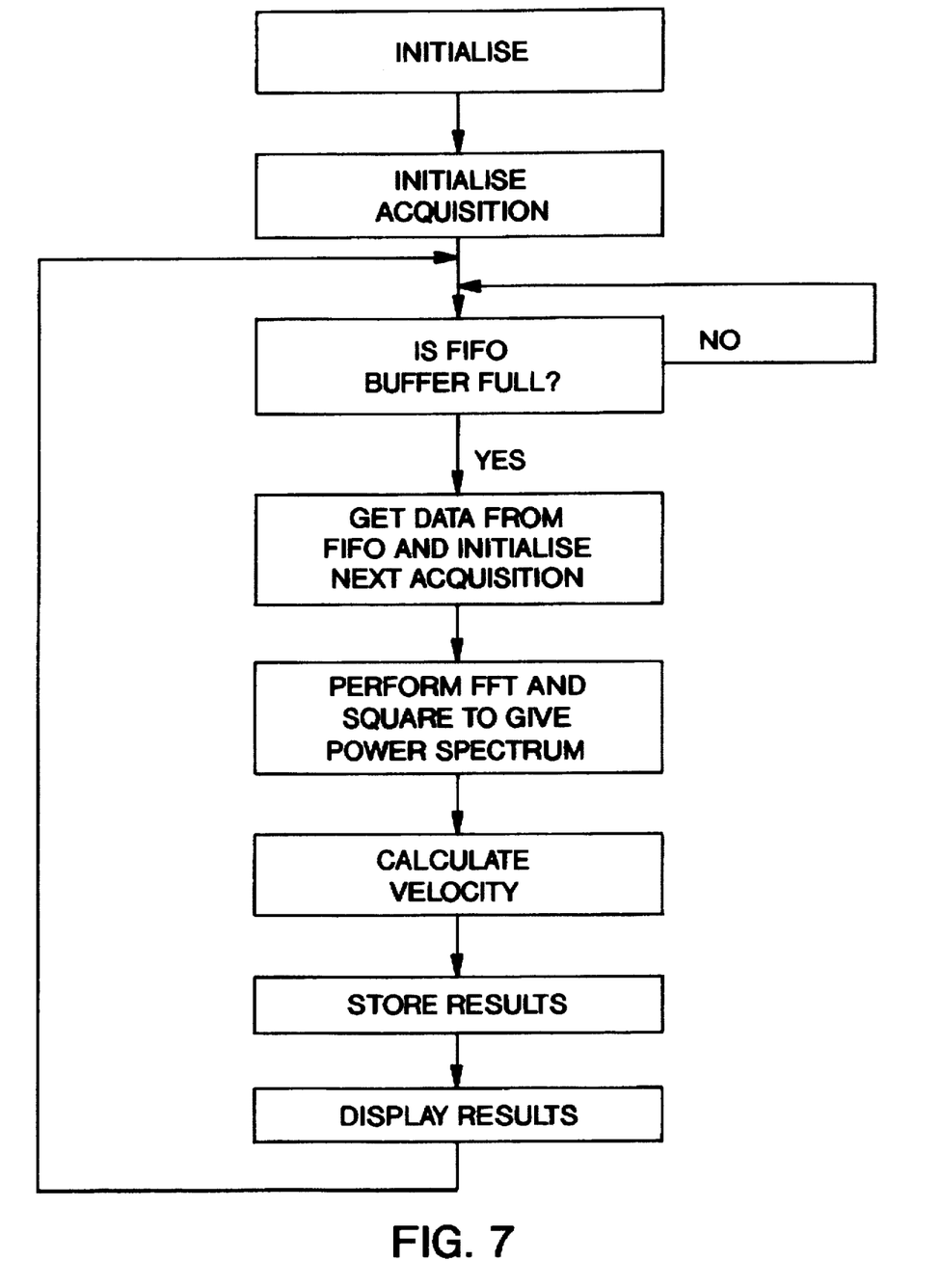
FIG. 7 is a flow chart showing the general mode of operation of the computer software.
Figure 8:
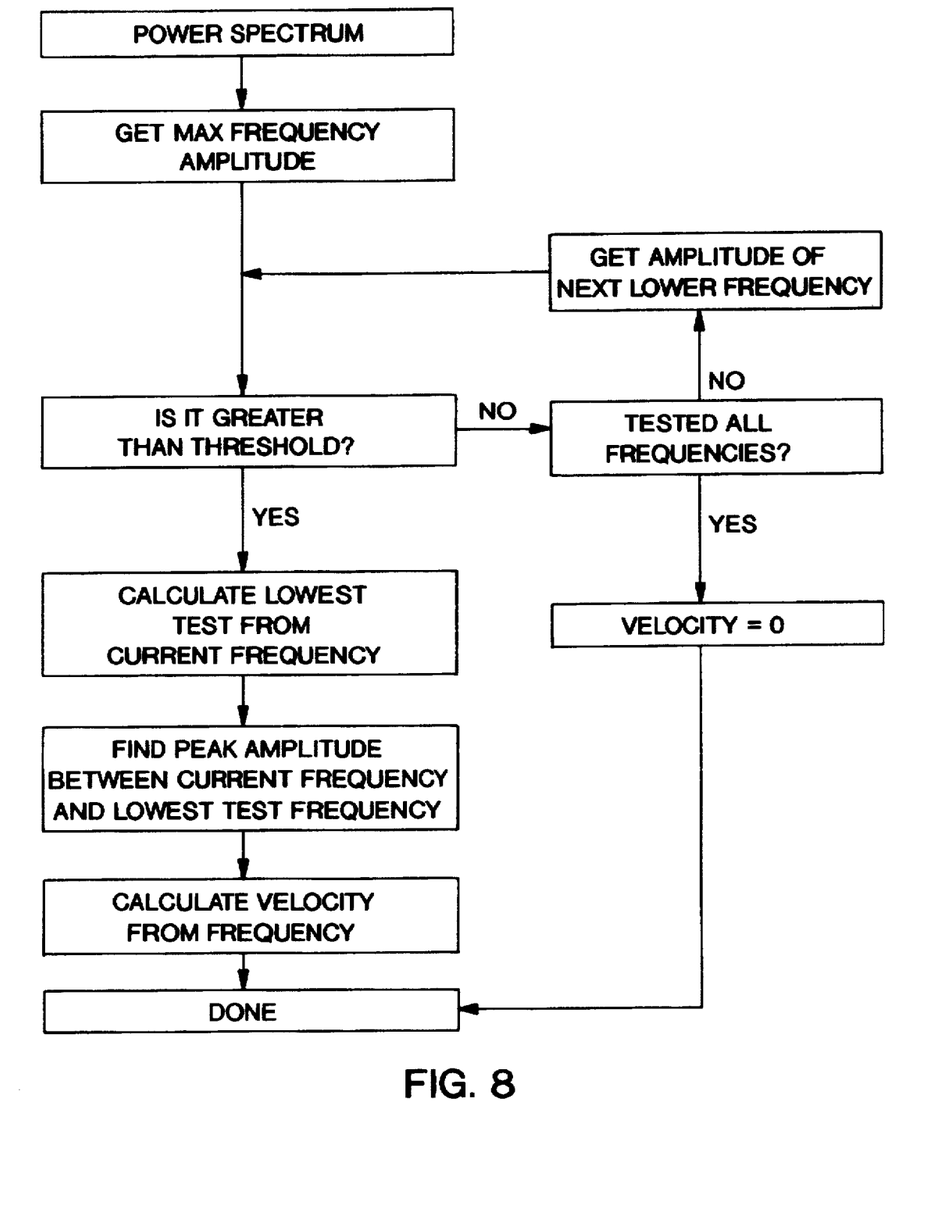
FIG. 8 is a flow chart showing the method of calculation of the velocity of the blood cells.

The computer software now takes the digitised data and performs an FFT (Fast Fourier Transformation) from which the power spectrum is computed and the frequency of the peak in the power spectrum (or the maximum frequency above a certain power threshold) is detected and used to calculate the velocity of the blood cells in a particular capillary. The information analysed by the computer can be displayed graphically on a monitor 10. The general method of operation of the computer software is shown in the flow chart of FIG. 7 and the method of calculating the velocity of the blood cells is shown in the flow chart of FIG. 8.

In a practical embodiment, the ADC 7 is a type AD7870JN manufactured by Analog Devices and the FIFO 8 comprises two type AM7201-50RC devices produced by Advanced Micro Devices.

The image formed by lens L2 is also focussed (via beam splitter BS1/F1 and a second filter F2) on to the CCD array of camera 3. This may be a high-resolution, high-sensitivity, monochrome XC-75CE camera produced by Sony Corporation. The camera output is fed to a video monitor 11 and also to a SVHS videorecorder 12. The videorecorder 12 can also be arranged to record the analogue output from the amplifier on to one of the audio tracks.

A frame grabber 11A can also be used to record snap-shots from the camera 3, or movie sequences, though this may be only of a selected area because of data bus bandwidth limitations. With, however, further technical developments in this area, it may become economically possible to record whole frames digitally at frame rate. The frame grabber 11A can be a model DT3851 produced by Data Translation.

The subject, for example, a finger 18, is illuminated by a 100 W halogen light source 13 via a fiber optic cable 14, a lens 15 and a green or blue/green filter 16. Green or blue-green light is used since this maximizes the contrast between the erythrocytes and the tissue, the CCD camera 3 is most sensitive in this region and the photodiode 5 is not very sensitive to green. The lens 15 may be replaced by a shaped acrylic rod and the filter 16 may be a BG-40 Schott glass blue/green filter to enhance contrast.

The subject can be positioned and focussed by the operator using an XYZ micropositioner stage 17. Alternatively, the subject can be maintained stationary and the instrument as a whole moved using a micropositioner. The use of the audio signal which is generated can enable the operator to locate more readily the point of maximum signal strength.

The software which is used may be such that the location of the capillaries can be determined by analysing the data from the frame grabber 11A. The instrument may thus be arranged to scan over each capillary area to find the point of maximum signal strength and the software will be such that the image will be monitored continuously for any movement of the subject.

There are basically three sources of movement:

a) involuntary muscle movements, b) respiration movements, and c) pulsatile cardiac pressure wave movements.

The first two types of movement are relatively easy to prevent mechanically by suitable fixing of the subject to the stage 17. The third are more difficult and are quite small movements. In addition, the subject cannot be clamped too close to the measurement area without disturbing the flow which is being measured.

To overcome this, the video image can be captured and a two-dimensional cross-correlation or other function used to determine the relative movement of the image. Cross-correlation is a standard technique and details of the method of carrying out this procedure can readily be ascertained from the text books on image/signal processing. This information can then be used to offset the position of the probing area. As the heartbeat is typically about 1 Hz , a quite high processing rate will be required.

Before carrying out a measurement, a drop of liquid paraffin is preferably placed on the relevant part of the finger 18. This serves to reduce surface reflections. The liquid paraffin should be at skin temperature before application to avoid any unwanted disturbances to blood flow.

The finger 18 is held securely in position and a perpendicular capillary loop is positioned under the laser beam.

The capillary selected (which is viewed using the camera 3) should be one where there is little surface reflection of the laser beam since too much surface reflection will result in feed-back into the laser causing a lot of "noise". Too much surface reflection may also cause tissue surface movements to dominate the reflected signal. When the beam is moved off the capillary, a "zero" flow or close to zero flow should be shown with little noise.

The operator should position the laser beam over the top of the arterial or venous limb and should avoid the apex of the capillary, since this may cause a doubling of the measured velocity by the homodyne mixing of the laser radiation reflected by blood cells travelling in opposite directions in the two limbs.

Figure 3:
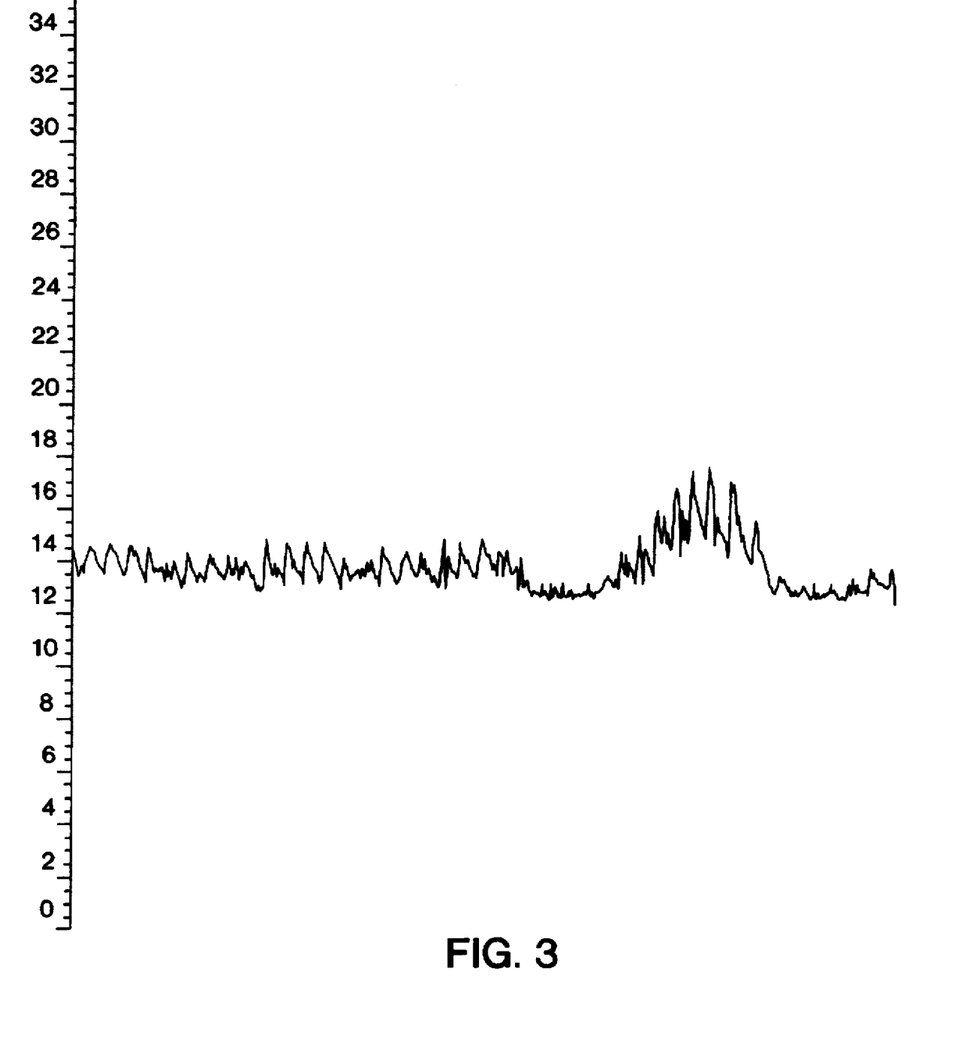
FIG. 3 shows a typical Doppler burst signal after it has been filtered.

FIG. 3 shows a typical Doppler burst signal after it has been filtered and each burst may well correspond to the passage of a single blood cell.

Figure 4:
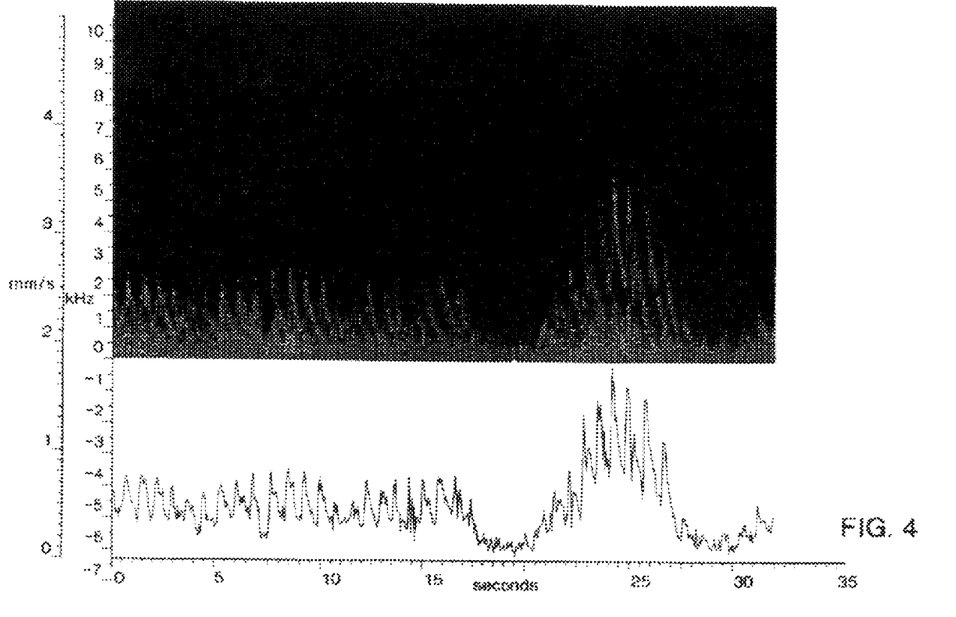
FIG. 4 shows the processed capillary velocity.

The processed capillary velocity is shown in FIG. 4 and the pulsatile nature of the velocity, due to the cardiac cycle, is to be noted. The flat section about two thirds of the way along the trace is signal drop-out, because the blood cell velocity has fallen to zero. This low-frequency variability is termed 'vasomotion'.

Figure 5:
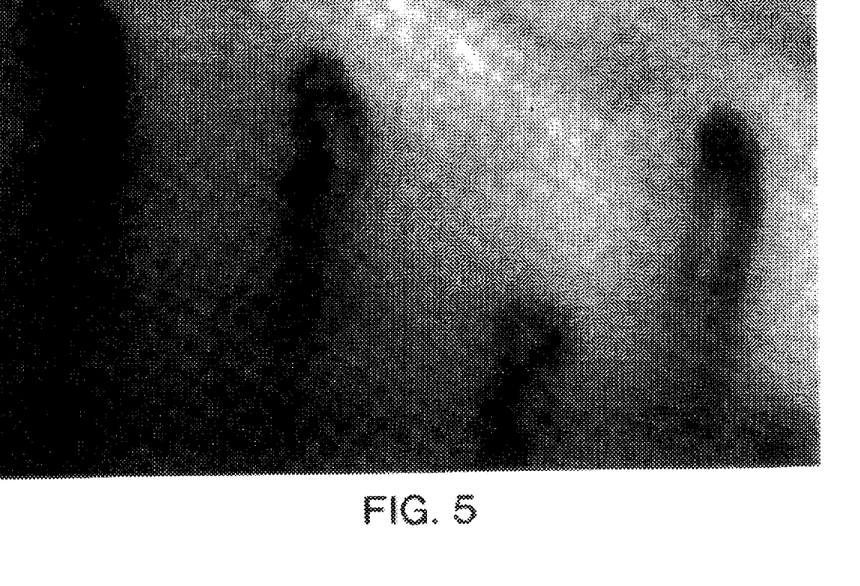
FIG. 5 shows capillaries at the nailfold, where they lie parallel to the surface.
Figure 6:
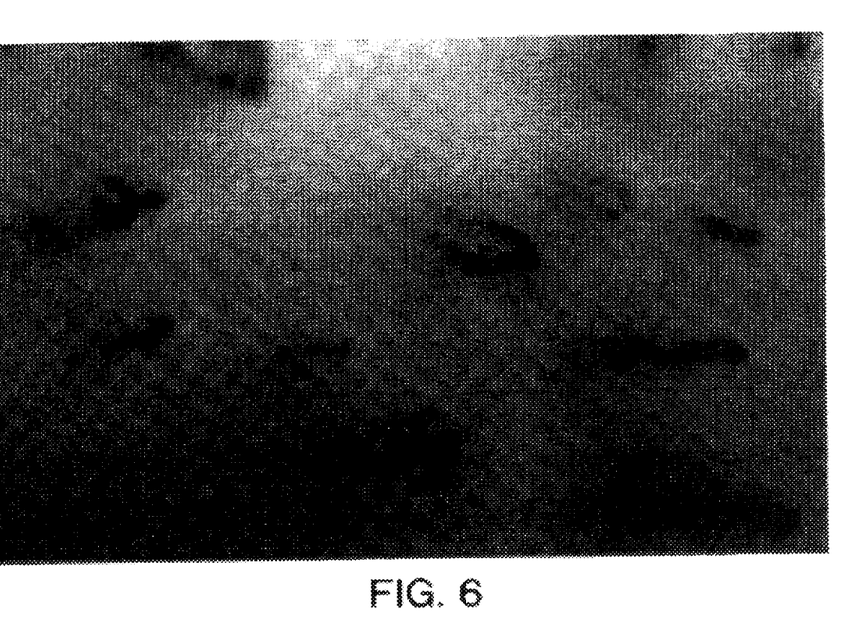
FIG. 6 shows capillaries from the back of the finger.

FIG. 5 shows the capillaries at the nailfold where they lie parallel to the surface at a magnification of about 500 times. This is to be compared to FIG. 6 which shows capillaries from the back of the finger at a magnification of about 250 times. It is to be noted that, in FIG. 6, only the apical part of the capillary is visible for most capillaries.

The blood cells travelling along the arterial or venous limb of a selected capillary which is perpendicular to the skin surface will, in effect, form an erythrocyte column moving with a velocity component perpendicular to the object plane. The laser radiation (which has been focussed to a spot size of the order of 10 microns in diameter) is scattered in all directions, mostly in the forward direction. All the scattered radiation will be Doppler-shifted, the actual amount of shift being dependant on the scattering angle with the maximum frequency shift occurring for directly back-scattered radiation. The laser radiation scattered through 180° will thus be effected by a Doppler shift and is collected by lens L1 and focussed on to the image plane 6 of the detector 5 via the beam splitter BS1/F1, mirror M1, beam splitter BS2 and mirror M2. The actual shift in frequency is directly proportional to the refractive index of blood plasma and to the velocity of the scattering blood cell(s). It is inversely proportional to the wavelength of the laser source.

At the same time, some of the surrounding radiation will also be back-scattered by some of the surrounding tissue and this 180° back-scattered radiation (which has not been subjected to a Doppler shift) will also be collected by the lens L1 and focussed on to the image plane 6 of the detector 5 via the beam splitter BS1/F1, mirror M1, beam splitter BS2 and mirror M2. The autodyne beating of the two optical signals at the detector will then produce the electrical signal (analysed by the computer 9) where the frequency of the ac component is directly proportional to the blood flow velocity.

The initial laser frequency=speed of light/wavelength, i.e. approximately $3 \times 10^8 / 780 \times 10^{-9}$=approx. $3.8 \times 10^{14}$ Hz. The Doppler shifts typically measured are around 3 kHz and the instrument of the present invention may thus have a measurement range of from 150 Hz to 50 kHZ.

I claim:

1. An instrument for use in the determination of blood cell velocity in a capillary in a tissue by a laser Doppler technique, said instrument comprising:

means for generating a laser beam;

means for directing the laser beam on to a surface of the tissue so as to impinge on a capillary within which blood cells are traveling with a component of velocity substantially perpendicular to the surface of the tissue;

a camera having an image plane for observing impingement of the laser beam on the surface;

means for measuring the velocity by detecting directly back-scattered laser radiation; and a lens system which collects the back-scattered laser beam and focuses the Doppler-shifted back-scattered radiation on to a photodetector via at least one beam splitter, said lens system also serving to effect focussing of radiation back-scattered by surrounding tissue and not subjected to Doppler-shifting.

2. An instrument as claimed in claim 1, which includes two beam splitters and two mirrors for directing the Doppler-shifted back-scattered radiation on to the photodetector.

3. An instrument as claimed in claim 1, comprising:

means for producing an electrical signal in the photodetector having a frequency component proportional to the blood cell velocity in response to autodyne beating of Doppler-shifted and non-Doppler shifted radiation signals.

4. An instrument as claimed in claim 3, which includes an ADC (Analogue to Digital Converter) to which the output from the photodetector is fed and a FIFO (First In First Out Buffer) connected to the ADC and in which the output of the ADC is buffered, said ADC including means for amplifying and bandwidth limiting the photodetector output before conversion by the ADC.

5. An instrument as claimed in claim 1, in which means are provided for illuminating the capillary by means of green light or blue/green light, and in which the green or blue/green light reflected from the capillary is collected by the objective lens and focussed on the image plane of the camera.

* * * * *